(12) United States Patent
Ziegler et al.

(10) Patent No.: US 10,254,257 B2
(45) Date of Patent: Apr. 9, 2019

(54) ESD PROTECTED TUBING FOR REMOVING CHARGE FROM LUMEN

(71) Applicant: Agilent Technologies, Inc., Santa Clara, CA (US)

(72) Inventors: Tony Ziegler, Steinfeld (DE); Stefan Falk-Jordan, Karlsruhe (DE)

(73) Assignee: Agilent Technologies, Inc., Santa Clara, CA (US)

( * ) Notice: Subject to any disclaimer, the term of this patent is extended or adjusted under 35 U.S.C. 154(b) by 249 days.

(21) Appl. No.: 15/107,337

(22) PCT Filed: Dec. 23, 2013

(86) PCT No.: PCT/IB2013/061292
§ 371 (c)(1),
(2) Date: Jun. 22, 2016

(87) PCT Pub. No.: WO2015/097498
PCT Pub. Date: Jul. 2, 2015

(65) Prior Publication Data
US 2017/0003256 A1    Jan. 5, 2017

(51) Int. Cl.
| | |
|---|---|
| *G01N 30/20* | (2006.01) |
| *F16L 11/127* | (2006.01) |
| *G01N 30/60* | (2006.01) |
| *B01D 15/24* | (2006.01) |
| *G01N 30/74* | (2006.01) |
| *G01N 30/80* | (2006.01) |
| *G01N 30/02* | (2006.01) |

(52) U.S. Cl.
CPC ......... *G01N 30/6052* (2013.01); *B01D 15/24* (2013.01); *F16L 11/127* (2013.01); *G01N 30/74* (2013.01); *G01N 30/80* (2013.01); *G01N 2030/027* (2013.01)

(58) Field of Classification Search
CPC . B01D 15/24; F16L 11/127; G01N 2030/027; G01N 30/6052; G01N 30/74; G01N 30/80
See application file for complete search history.

(56) References Cited

U.S. PATENT DOCUMENTS

| | | | |
|---|---|---|---|
| 3,070,132 | A | 12/1962 | Sheridan |
| 3,580,983 | A | 5/1971 | Jackson |

(Continued)

FOREIGN PATENT DOCUMENTS

| | | |
|---|---|---|
| CN | 2895950 | 5/2007 |
| CN | 201014075 | 1/2008 |

(Continued)

OTHER PUBLICATIONS

International Search Report dated Aug. 5, 2014 for related International Application No. PCT/IB2013/061292.

*Primary Examiner* — Randy Gibson
*Assistant Examiner* — Gedeon M Kidanu

(57) ABSTRACT

An electrostatic discharge protected device for conducting a fluid through at least one lumen includes a tubing having a hollow interior defining the at least one lumen. The tubing includes an electrically conductive section configured for conducting electric charge, generated within the at least one lumen when the fluid flows through the at least one lumen, away from the at least one lumen.

20 Claims, 3 Drawing Sheets

(56) References Cited

U.S. PATENT DOCUMENTS

| | | | | |
|---|---|---|---|---|
| 3,780,208 A | * | 12/1973 | Whittaker | F16L 11/127 174/47 |
| 4,982,597 A | | 1/1991 | Berger | |
| 5,076,242 A | * | 12/1991 | Parker | F02M 55/007 123/468 |
| 5,614,589 A | * | 3/1997 | Niznik | C08L 51/04 525/125 |
| 5,898,560 A | * | 4/1999 | Flaynik, Jr. | B01D 35/02 361/215 |
| 6,354,331 B1 | * | 3/2002 | Fisher | B29C 47/0023 138/104 |
| 6,679,297 B1 | * | 1/2004 | Nishi | F16L 11/12 138/137 |
| 8,411,405 B2 | * | 4/2013 | Blackburn | H05F 3/025 361/215 |
| 9,046,201 B1 | * | 6/2015 | Theis | F16L 11/08 |
| 9,056,264 B2 | * | 6/2015 | Hahn | B01D 15/22 |
| 2002/0029619 A1 | * | 3/2002 | Lee | G01N 30/82 73/61.52 |
| 2003/0098085 A1 | * | 5/2003 | Ito | B32B 1/08 138/137 |
| 2003/0150503 A1 | * | 8/2003 | Ito | F16L 11/04 138/137 |
| 2007/0259147 A1 | * | 11/2007 | Boudry | B32B 1/08 428/36.8 |
| 2010/0116941 A1 | * | 5/2010 | Ciolcyzk | F16L 9/125 244/135 R |
| 2012/0024411 A1 | * | 2/2012 | Hahn | B01D 15/22 138/109 |

FOREIGN PATENT DOCUMENTS

| | | |
|---|---|---|
| EP | 0309596 A1 | 4/1989 |
| EP | 0530507 A1 | 3/1993 |
| GB | 1041255 A | 9/1966 |
| WO | 96/13680 A1 | 5/1996 |

\* cited by examiner

ESD PROTECTED TUBING FOR REMOVING CHARGE FROM LUMEN

RELATED APPLICATIONS

This application is the national stage of International Application No. PCT/IB2013/061292, filed Dec. 23, 2013, titled "ESD PROTECTED TUBING FOR REMOVING CHARGE FROM LUMEN," the content of which is incorporated herein by reference in its entirety.

BACKGROUND ART

The present invention relates to an electrostatic discharge protected device for conducting a fluid through at least one lumen, to a fluid separation apparatus, and to a method of conducting a fluid through at least one lumen with electrostatic discharge protection.

U.S. Pat. No. 3,580,983 discloses that nonsparking tubes can be fabricated from polymers which are susceptible of acquiring an electrostatic charge upon frictionally contacting other bodies or surfaces such as textile elements. U.S. Pat. No. 3,580,983 furthermore discloses a conductive line tubing manufactured by extruding from a mass of flexible plastic material an elongated tube contemporaneous with the extrusion of an elongated electrically conductive plastic filament that is secured to said tube in superimposed relationship piggyback arrangement.

U.S. Pat. No. 5,614,589 discloses a transparent, antistatic thermoplastic composition and methods of making the same.

In liquid chromatography, a fluidic sample (mobile phase) may be pumped through conduits and a column comprising a material (stationary phase) which is capable of separating different components of the fluidic analyte. Such a material, so-called beads which may comprise silica gel, may be filled into a column tube which may be connected to other elements (like a sampling unit, a flow cell, containers including sample and/or buffers) by conduits.

The flow path of the mobile phase typically comprises plural individual components coupled together, which, in turn, might also be comprised of individual sub-components. Such a fluidic connection may be accomplished by tubings conducting the fluid between the respective components.

However, when fluid, in particular at least partially non-polar fluid, flows through such a conduit or tubing in particular with high passing speed of liquid molecules through a given diameter within the tubing, it may happen that electric charge is generated by friction in an interior of the tubing and accumulates on the tubing. This may involve safety risks.

DISCLOSURE

It is an object of the invention to provide a tubing for conducting fluid which is safe in operation.

According to an exemplary embodiment of the present invention, an electrostatic discharge protected device for conducting a fluid (for instance a non-polar fluid, wherein the term "fluid" may denote any liquid and/or gaseous medium optionally comprising a solid contribution) through at least one lumen is provided, wherein the device comprises a tubing having a hollow interior defining the at least one lumen, wherein the tubing comprises an electrically conductive section configured for conducting electric charge, generated within the at least one lumen when the fluid flows through the at least one lumen, away from the at least one lumen.

According to another exemplary embodiment, a fluid separation apparatus for separating a fluidic sample into a plurality of fractions is provided, wherein the apparatus comprises a fluid drive unit configured for driving a fluid comprising a mobile phase and the fluidic sample in the mobile phase along a fluidic path, a separation unit arranged within the fluidic path and configured for separating the fluidic sample into the plurality of fractions, and a device having the above mentioned features for conducting the fluid along at least a portion of the fluidic path.

According to still another exemplary embodiment, a method of conducting a fluid (for instance a non-polar fluid) through at least one lumen with electrostatic discharge protection is provided, wherein the method comprises conducting the fluid through a hollow interior of a tubing defining the at least one lumen, and conducting electric charge, generated within the at least one lumen when the fluid flows through the at least one lumen, away from the at least one lumen by an electrically conductive section of the tubing.

According to yet another exemplary embodiment, a method of implementing a device having the above mentioned features as a fluidic connection downstream of a flow cell of a liquid chromatography apparatus is provided.

According to an exemplary embodiment, a tubing for conducting fluid is equipped with an electrically conductive section which, in combination with a specific configuration of the remaining material of the tubing, is specifically configured to allow electric charge carriers generated by friction between the fluid flowing through the lumen and the inner wall of the tubing to propagate radially through the tubing wall so as to be conducted away (for instance towards an electric ground potential) from the inside of the tubing. Advantageously, it has turned out that charge carriers generated within the lumen and being therefore not easily accessible can be removed by a mechanism of conducting them through the tubing. In particular, this can be accomplished by an appropriate choice of geometrical properties (such as radial thickness) and/or by an appropriate choice of the material properties (in particular the value of the electric conductivity) of the electrically conductive section and the remaining portion of the tubing. Thus, in particular an inside pure ESD tubing is provided according to an exemplary embodiment.

In the following, further embodiments of the electrostatic discharge protected device, the fluid separation apparatus, and the methods will be explained.

In an embodiment, the tubing is configured so that the electric charge is conducted away from the at least one lumen through at least a part of the wall of the tubing, in particular through the entire wall of the tubing. Thus, a trajectory according to which electric charge is conducted away may be first radially through the tubing and subsequently along an axial direction of the tubing.

In an embodiment, the tubing comprises a chemically inert section delimiting the entire lumen and forming an intermediate structure separating the at least one lumen from the electrically conductive section for preventing direct contact between the fluid and the electrically conductive section. It has turned out that the above mentioned radial motion of the electric charge carriers through the tubing is not only possible when the electrically conductive section extends radially up to the lumen but surprisingly also in the case of a sufficiently thin intermediate structure of pure inert but poorly electrically conductive material (such as a polymer) bridging the lumen with regard to the electrically conductive section. This makes it possible to configure the intermediate structure from a material being inert (for instance chemically inert and/or bioinert) against the fluid so that it can be efficiently suppressed that the fluid dissolves any components out of the wall of the tubing. Hence, impurification and toxication of the fluid can be prevented. At the same time, this increases the freedom of selecting the material of the electrically conductive section to properly fulfil its charge draining task without the need to consider constraints in terms of inertness.

In an embodiment, the chemically inert section is configured, in particular in terms of dimension and/or electric conductivity, for electrically conducting the generated electric charge from the at least one lumen through the intermediate structure and towards the electrically conductive section. Hence, even quite small values of the electric conductivity of an inert material may be sufficient to allow the generated charge carriers (such as electrons) to pass the chemically inert section.

In an embodiment, the chemically inert section has, at least at a portion where the chemically inert section is surrounded by the electrically conductive section, a radial thickness in a range between approximately 0.05 mm and approximately 0.4 mm, in particular in a range between approximately 0.10 mm and approximately 0.16 mm. For example, it has turned out to be surprisingly possible to conduct the electric charge through a 0.13 mm thick intermediate structure of PTFE. It has turned out that in particular many polymer materials have a slight electrical conductivity which is sufficient to transport the electric charge carriers (such as electrons) through the mentioned small thicknesses. The radial thickness may be up to 1 mm, or more, if the tubing is used for high flow applications such as applications in process engineering, preparative systems, etc.

In an embodiment, the electrically conductive section radially extends from the at least one lumen to an external surface of the tubing. In such embodiments, the full wall thickness is bridged by the electrically conductive section so that an uninterrupted electric charge flow through the electrically conductive material can take place. Care should be taken in such an embodiment that the electrically conductive material does not show an undesired interaction with the fluid. For instance, the material of the electrically conductive section should then be selected so that the conducted fluid does not dissolve harmful components out of the tubing, and that also the fluid flowing through the lumen of the tubing is not negatively influenced by the material of the electrically conductive section contacting the flowing fluid.

In an embodiment, the tubing comprises an optically transparent section configured for enabling an external inspection of the conducted fluid within the at least one lumen. For example, the entire tubing with the exception of the electrically conductive material can be made of an optically transparent material through which a user can inspect the fluid flowing in the lumen. For example in terms of liquid chromatography, the presence of air bubbles or the like in the flowing fluid may be indicators of a problem in the liquid separation setup, so that the option of monitoring the fluid flow may be highly advantageous.

In an embodiment, the entire lumen is delimited by the optically transparent section, and the electrically conductive section is arranged to surround part of the optically transparent section so that the electric charge is at least partially electrically conducted from the at least one lumen via the optically transparent section to the electrically conductive section. Many polymers show at the same time an optically transparent property as well as an inertness against chemical fluids (such as solvents for liquid chromatography) and biological fluids (such as fluidic samples to be separated by liquid chromatography) and is therefore particularly suitable to be used as the basis for the formation of the tubing. Only the locally required electrical conductivity of the tubing is then provided by the electrically conductive section. A corresponding tubing can be manufactured with reasonable effort and provides all properties desired by a user.

In an embodiment, the electrically conductive section is configured as an axially extending annular segment of the tubing. Forming the electrically conductive section as an axially continuous structure allows to transport the generated charge carriers towards an electric ground potential, even over a relatively large distance parallel to the flowing fluid. By providing the electrically conductive section only along a part of the circumference of the tubing allows to maintain the visual inspectability along the entire axial extension of the tubing.

In an embodiment, the annular segment extends over an annular range between approximately 30° and approximately 180°, in particular between approximately 80° and approximately 120°. This allows to obtain an electrically conductive path with a sufficiently low value of the ohmic resistance. At the same time this allows to keep a sufficient angular portion of the perimeter of the tubing optically transparent to render optical inspection of the interior of the tubing possible.

In an embodiment, at least the part of the material of the tubing being in direct contact with the fluid conducted through the at least one lumen is chemically inert against a non-polar solvent (such as n-hexane) conducted as at least part of the fluid through the at least one lumen. A non-polar solvent is particularly problematic in terms of electrostatic discharges, because this type of fluid is incapable to efficiently transport away all generated electric charge in a neutral way. At the same time, such a solvent may have the tendency to chemically attack electrically conductive material. Contacting such kind of fluid only to an inert material while maintaining a discharge current flow through the tubing wall provides an ESD protection and prevents an undesired dissolution of particles particularly of the electrically conductive section into the non-polar solvent.

In an embodiment, the electrically conductive section is integrated within the wall of the tubing, in particular in a protrusion free fashion. Thus, in particular the exterior surface of the tubing may be smooth and therefore free of protrusions so that the tubing with embedded conductive portion is not in the danger to get mechanically caught or stuck with any other components of a fluid separation apparatus, thereby improving the operation safety of the device.

In an embodiment, the device comprises a ground connector configured to be connected to the electrically conductive section for discharging the electrostatic charge towards ground. Such a ground connector may be an electrically conductive component (for instance comprising a circumferential electric isolation for the sake of safety) which may be brought in physical contact with the electrically conductive section of the tubing to thereby close an electric path from the electrically conductive section towards the electric ground potential for continuous removal of the electric charge carriers. For instance, such a ground connector may be a cone, disk, or a clamp connecting the ESD strip (i.e. the electrically conductive section) safely to ground.

In an embodiment, the device comprises an electrically conductive flange for mechanically coupling the device to a housing and simultaneously electrically coupling the electrically conductive section to the housing. The housing itself may be grounded and may be made, for instance, of a metallic material. The housing may form part of the fluid separation apparatus. The mentioned flange may for instance be a fitting for screwing the device to the housing.

In an embodiment, an external diameter of the tubing is smaller than approximately 8 mm, in particular is smaller than approximately 4 mm. In an embodiment, a thickness of a wall of the tubing is in a range between approximately 0.3 mm and approximately 1.5 mm. Such tubings are particularly appropriate for the pressures and flow rates occurring in fluid separation apparatuses such as a liquid chromatography apparatus.

In an embodiment, at least one of the group consisting of the chemically inert section and the optically transparent section (in particular a chemically inert and simultaneously optically transparent section) is made of a polymer, in particular a fluoropolymer, more particularly (pure or modified) polytetrafluoroethylene (PTFE) or fluorinated ethylene-propylene polymer (FEP). PTFE is particularly appropriate in view of its highly advantageous bending properties, i.e. its property of being highly flexible without the risk of breakage. FEP is particularly appropriate in view of its pronounced inertness against chemical and biological fluids. Other polymer materials are possible as well, such as PEEK (polyetheretherketone).

In an embodiment, the electrically conductive section has a value of the ohmic resistance per length of the tubing of less than approximately 2 MΩ/m, in particular in a range between approximately 100 kΩ/m and approximately 1 MΩ/m. For example, carbon black or graphite like carbon are appropriate electrically conductive materials which may be embedded in a polymer matrix to thereby form the electrically conductive section. Advantageously, the polymer in which such a carbon-based conductor is embedded may be the same material than that of the rest of the tubing. This allows to manufacture an integrally formed and therefore robust and mechanically flexible tubing constituting the electrostatic discharge protected device.

In an embodiment, the tubing has a circular or a polygonal outer circumference, in particular along the entire extension of the tubing. For instance, the perimeter may be shaped as a circle, a triangle, a rectangle (in particular a square), etc.

In an embodiment, the device further comprises an optical source (such as a light source) configured for generating primary optical light for propagation through a first part of the optically transparent section, the at least one lumen, and a second part of the optically transparent section, and comprises an optical detector (such as a photocell) arranged for detecting secondary optical light being transmitted through the fluid upon being irradiated with the primary optical light. Therefore, in view of the partially optically transparent property of the tubing, it is possible to measure the absorption or transmission (refracted light included in this contemplation) of liquids or gases in the tubing upon irradiating the fluid in the lumen with primary light. Such an optical arrangement may be configured as a refraction sensor or as a fraction delay sensor (which may be arranged upstream of a fractioner valve), as used for liquid chromatography applications for determining information concerning flow times of specific sections in the flowing fluid.

In an embodiment, the fluid comprises or consists of a non-polar solvent. In particular for non-polar solvents (such as n-hexane), the intrinsic property of the fluid flowing through the lumen of conducting away generated charge carriers from the border wall between tubing and fluid may be highly limited, or may be even close to zero. Thus, in particular for such kind of solvents, the integration of the electrically conductive section into the tubing of the wall and the configuration of the tubing so as to transport the charge carriers through the wall out of the tubing is of great advantage.

In an embodiment, the device is implemented as fluidic connection between the flow cell and a fractioner of the liquid chromatography apparatus. Particularly this portion of the liquid chromatography apparatus has turned out as a week point in terms of electrostatic discharges.

The separation unit may be filled with a separating material. Such a separating material which may also be denoted as a stationary phase may be any material which allows an adjustable degree of interaction with a sample fluid so as to be capable of separating different components of such a sample fluid. The separating material may be a liquid chromatography column filling material or packing material comprising at least one of the group consisting of polystyrene, zeolite, polyvinylalcohol, polytetrafluoroethylene, glass, polymeric powder, silicon dioxide, and silica gel, or any of above with chemically modified (coated, capped etc) surface. However, any packing material can be used which has material properties allowing an analyte passing through this material to be separated into different components, for instance due to different kinds of interactions or affinities between the packing material and fractions of the analyte.

At least a part of the separation unit may be filled with a fluid separating material, wherein the fluid separating material may comprise beads having a size in the range of essentially 1 µm to essentially 50 µm. Thus, these beads may be small particles which may be filled inside the separation section of the microfluidic device. The beads may have pores having a size in the range of essentially 0.01 µm to essentially 0.2 µm. The fluidic sample may be passed through the pores, wherein an interaction may occur between the fluidic sample and the pores.

The separation unit may be a chromatographic column for separating components of the fluidic sample. Therefore, exemplary embodiments may be particularly implemented in the context of a liquid chromatography apparatus.

The fluid separation apparatus may be configured to conduct a liquid mobile phase through the separation unit. As an alternative to a liquid mobile phase, a gaseous mobile phase or a mobile phase including solid particles may be processed using the fluid separation apparatus. Also materials being mixtures of different phases (solid, liquid, gaseous) may be processed using exemplary embodiments. The fluid separation apparatus may be configured to conduct the mobile phase through the system with a high pressure, particularly of at least 600 bar, more particularly of at least 1200 bar.

The fluid separation apparatus may be configured as a microfluidic device. The term "microfluidic device" may particularly denote a fluid separation apparatus as described herein which allows to convey fluid through microchannels having a dimension in the order of magnitude of less than 500 µm, particularly less than 200 µm, more particularly less than 100 µm or less than 50 µm or less.

Exemplary embodiments may be implemented in a sample injector of a liquid chromatography apparatus which sample injector may take up a sample fluid from a fluid container and may inject such a sample fluid in a conduit for supply to a separation column. During this procedure, the sample fluid may be compressed from, for instance, normal pressure to a higher pressure of, for instance several hundred bars or even 1000 bar and more. An autosampler may automatically inject a sample fluid from the vial into a sample loop (alternatively, a fixed loop concept may be applied). A tip or needle of the autosampler may dip into a fluid container, may suck fluid into the capillary and may then drive back into a seat to then, for instance via a switchable fluidic valve, inject the sample fluid towards a sample separation section of the liquid chromatography apparatus.

The fluid separation apparatus may be configured to analyze at least one physical, chemical and/or biological parameter of at least one component of the sample fluid in the mobile phase. The term "physical parameter" may particularly denote a size or a temperature of the fluid. The term "chemical parameter" may particularly denote a concentration of a fraction of the analyte, an affinity parameter, or the like. The term "biological parameter" may particularly denote a concentration of a protein, a gene or the like in a biochemical solution, a biological activity of a component, etc.

The fluid separation apparatus may be implemented in different technical environments, like a sensor device, a test device, a device for chemical, biological and/or pharmaceutical analysis, a capillary electrophoresis device, a liquid chromatography device, a gas chromatography device, an electronic measurement device, or a mass spectroscopy device. Particularly, the fluid separation apparatus may be a High Performance Liquid device (HPLC) device by which different fractions of an analyte may be separated, examined and analyzed.

An embodiment of the present invention comprises a fluid separation apparatus configured for separating compounds of a sample fluid in a mobile phase. The fluid separation apparatus may comprise a mobile phase drive, such as a pumping system, configured to drive the mobile phase through the fluid separation apparatus. A separation unit, which can be a chromatographic column, is provided for separating compounds of the sample fluid in the mobile phase. The fluid separation apparatus may further comprise a sample injector configured to introduce the sample fluid into the mobile phase, a detector configured to detect separated compounds of the sample fluid, a collector configured to collect separated compounds of the sample fluid, a data processing unit configured to process data received from the fluid separation apparatus, and/or a degassing apparatus for degassing the mobile phase.

Embodiments of the present invention might be embodied based on most conventionally available HPLC systems, such as the Agilent 1290 Series Infinity system, Agilent 1200 Series Rapid Resolution LC system, or the Agilent 1100 HPLC series (all provided by the applicant Agilent Technologies—see www.agilent.com—which shall be incorporated herein by reference).

One embodiment comprises a pumping apparatus having a piston for reciprocation in a pump working chamber to compress liquid in the pump working chamber to a high pressure at which compressibility of the liquid becomes noticeable. One embodiment comprises two pumping apparatuses coupled either in a serial (e.g. as disclosed in EP 309596 A1) or parallel manner.

The mobile phase (or eluent) can be either a pure solvent or a mixture of different solvents. It can be chosen e.g. to minimize the retention of the compounds of interest and/or the amount of mobile phase to run the chromatography. The mobile phase can also been chosen so that the different compounds can be separated effectively. The mobile phase might comprise an organic solvent like e.g. methanol or acetonitrile, often diluted with water. For gradient operation water and organic are delivered in separate bottles, from which the gradient pump delivers a programmed blend to the system. Other commonly used solvents may be isopropanol, tetrahydrofuran (THF), hexane, ethanol and/or any combination thereof or any combination of these with aforementioned solvents.

The sample fluid might comprise any type of process liquid, natural sample like juice, body fluids like plasma or it may be the result of a reaction like from a fermentation broth.

The fluid is preferably a liquid but may also be or comprise a gas and/or a supercritical fluid (as e.g. used in supercritical fluid chromatography—SFC—as disclosed e.g. in U.S. Pat. No. 4,982,597 A).

The pressure in the mobile phase might range from 2-200 MPa (20 to 2000 bar), in particular 10-150 MPa (100 to 1500 bar), and more particularly 50-120 MPa (500 to 1200 bar).

BRIEF DESCRIPTION OF DRAWINGS

Other objects and many of the attendant advantages of embodiments of the present invention will be readily appreciated and become better understood by reference to the following more detailed description of embodiments in connection with the accompanying drawings. Features that are substantially or functionally equal or similar will be referred to by the same reference signs.

Figure 1:
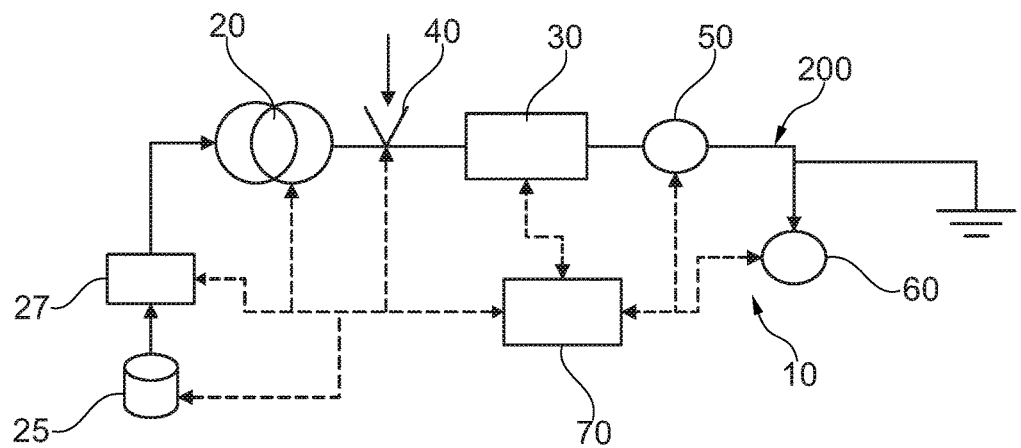
FIG. 1 shows a liquid separation apparatus in accordance with embodiments of the present invention, particularly used in high performance liquid chromatography (HPLC).

The illustration in the drawing is schematic.

Referring now in greater detail to the drawings, FIG. 1 depicts a general schematic of a liquid separation system 10. A pump 20 receives a mobile phase from a solvent supply 25, typically via a degasser 27, which degasses and thus reduces the amount of dissolved gases in the mobile phase. The pump 20—as a mobile phase drive—drives the mobile phase through a separating device 30 (such as a chromatographic column) comprising a stationary phase. A sampling unit 40 can be provided between the pump 20 and the separating device 30 in order to subject or add (often referred to as sample introduction) a sample fluid into the mobile phase. The stationary phase of the separating device 30 is configured for separating compounds of the sample liquid. A detector 50 is provided for detecting separated compounds of the sample fluid. A fractionating unit 60 can be provided for outputting separated compounds of sample fluid.

While the mobile phase can be comprised of one solvent only, it may also be mixed from plural solvents. Such mixing might be a low pressure mixing and provided upstream of the pump 20, so that the pump 20 already receives and pumps the mixed solvents as the mobile phase. Alternatively, the pump 20 might be comprised of plural individual pumping units, with plural of the pumping units each receiving and pumping a different solvent or mixture, so that the mixing of the mobile phase (as received by the separating device 30) occurs at high pressure and downstream of the pump 20 (or as part thereof). The composition (mixture) of the mobile phase may be kept constant over time, the so called isocratic mode, or varied over time, the so called gradient mode.

A data processing unit 70, which can be a conventional PC or workstation, might be coupled (as indicated by the dotted arrows) to one or more of the devices in the liquid separation system 10 in order to receive information and/or control operation. For example, the data processing unit 70 might control operation of the pump 20 (e.g. setting control parameters) and receive therefrom information regarding the actual working conditions (such as output pressure, flow rate, etc. at an outlet of the pump 20). The data processing unit 70 might also control operation of the solvent supply 25 (e.g. setting the solvent/s or solvent mixture to be supplied) and/or the degasser 27 (e.g. setting control parameters such as vacuum level) and might receive therefrom information regarding the actual working conditions (such as solvent composition supplied over time, flow rate, vacuum level, etc.). The data processing unit 70 might further control operation of the sampling unit 40 (e.g. controlling sample injection or synchronization of sample injection with operating conditions of the pump 20). The separating device 30 might also be controlled by the data processing unit 70 (e.g. selecting a specific flow path or column, setting operation temperature, etc.), and send—in return—information (e.g. operating conditions) to the data processing unit 70. Accordingly, the detector 50 might be controlled by the data processing unit 70 (e.g. with respect to spectral or wavelength settings, setting time constants, start/stop data acquisition), and send information (e.g. about the detected sample compounds) to the data processing unit 70. The data processing unit 70 might also control operation of the fractionating unit 60 (e.g. in conjunction with data received from the detector 50) and provide data back.

As can be taken from FIG. 1, fluid has to be conducted between the various components of the liquid separation system 10. In particular fluids having at least a non-polar component are prone to undesired electrostatic discharges. In order to overcome this risk, corresponding sections of the fluidic conduits shown in the liquid separation system 10 of FIG. 1 can be equipped with an electrostatic discharge protected device 200 as shown in FIG. 2 to FIG. 5 and FIG. 8. In particular downstream of a flow cell (as an embodiment of detector 50) and upstream of the fractionating unit 60/waste, such an electrostatic discharge protected device 200 is highly advantageous. An electrically conductive section of a tubing of the electrostatic discharge protected device 200 may be connected to an electric ground potential, as indicated schematically in FIG. 1.

Figure 2:
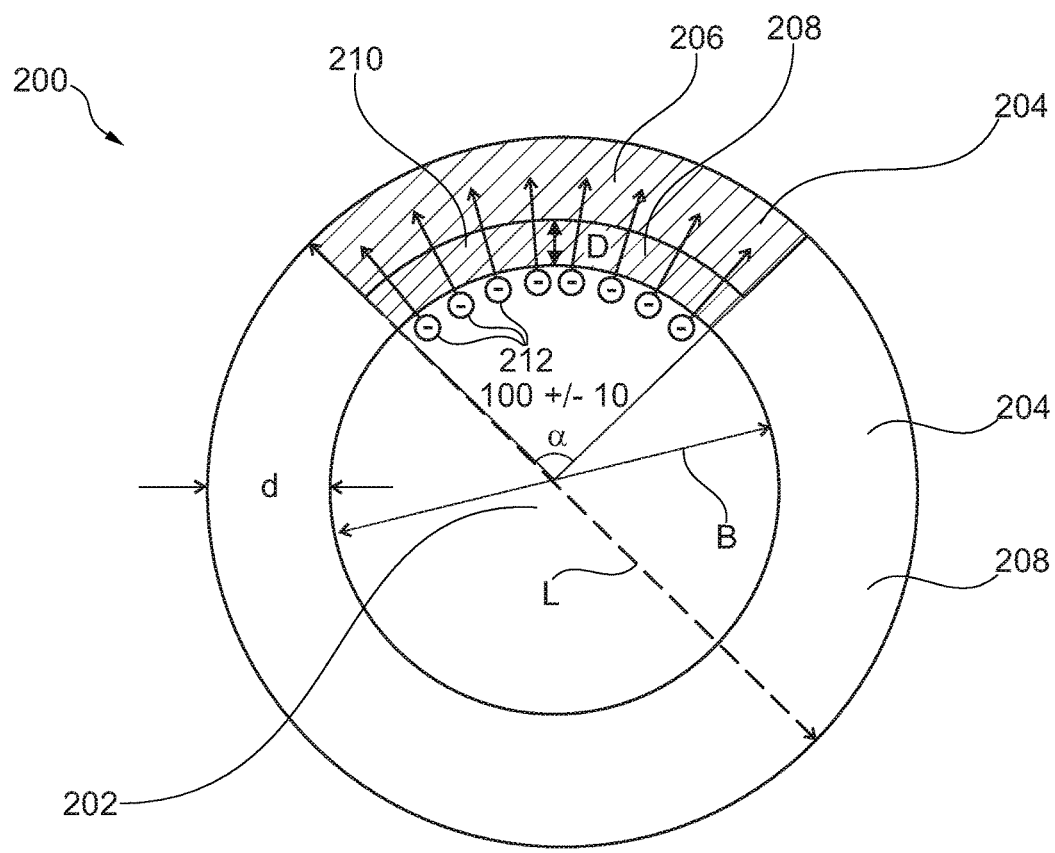
FIG. 2 to FIG. 5 illustrate cross-sectional views of electrostatic discharge protected devices for conducting a fluid through a lumen according to exemplary embodiments of the invention.

FIG. 2 illustrates a cross-sectional view of tubular electrostatic discharge protected device 200 for conducting a fluid through a lumen 202 according to an exemplary embodiment of the invention.

FIG. 2 shows the electrostatic discharge protected device 200 for conducting a non-polar liquid solvent through lumen 202 and comprises a hollow cylindrical tubing 204 having a hollow interior defining the lumen 202. The tubing 204 comprises an exterior annular segment configured as electrically conductive section 206, here embodied as electrically conductive carbon black particles embedded in a polymer matrix. The electrically conductive section 206 is capable of conducting electric charge 212—generated by friction within the lumen 202 when the non-polar liquid solvent flows through the lumen 202 perpendicular to a paper plane of FIG. 2—away from the lumen 202. The rest of the tubing 204 is configured as an optically transparent and chemically inert section 208 delimiting the entire lumen 202, made of the same polymer as the matrix of the electrically conductive section 206 and forming an intermediate structure 210 separating the lumen 202 from the electrically conductive section 206 mechanically, but not electrically, for preventing direct contact between the liquid solvent and the electrically conductive section 206. The optical transparency enables a user to perform an external inspection of the conducted liquid solvent within the lumen 202 from an exterior of the device 200. Advantageously, the optically transparent and chemically inert section 208 is configured for electrically conducting the generated electric charge 212 from the lumen 202 through the intermediate structure 210 and towards the electrically conductive section 206, as indicated by arrows in FIG. 2. This can be accomplished by an appropriate choice of the material of the mentioned polymer (optically transparent, sufficient electric conductivity) as well as of a thickness D (sufficiently small to allow flow of electric charge 212 through it, sufficiently large to prevent interaction between fluid and electrically conductive section 206) of the intermediate structure 210. As a polymer, it is appropriate to use PTFE, since this material is optically transparent, chemically inert and has a sufficient electric conductivity to allow the electric charge 212 to traverse the intermediate structure 210 towards the electrically conductive section 206. Thus, any risk of an electrostatic discharge can be overcome. In the shown embodiment, the thickness D can be selected advantageously to be in a range between 0.10 mm and 0.16 mm. Thus, the path of the electric charge 212 when being conducted away from the lumen 202 reaches from an inner wall of the tubing 204, via the intermediate structure 210 of relatively poor, but still sufficiently high electric conductivity towards the highly electrically conductive section 206, from where the electric charge 212 can be conducted perpendicular to the paper plane of FIG. 2 along an axial direction of the tubing 204, for instance towards an electric ground connection.

An external diameter L of the tubing 204 is 2.5 mm. A thickness d of a wall of the tubing 204 is 0.45 mm. The electrically conductive section 206 may have a value of the ohmic resistance per length of the tubing 204 of several 100 k$\Omega$/m (more generally in a range between 1 k$\Omega$/m to 1 M$\Omega$/m). A length of the tubing 204 (perpendicular to the paper plane of FIG. 2) may be between 10 cm and 5 m, and particularly between 50 cm and 3 m.

The electrically conductive section 206 is configured as an integral axially extending annular segment of the tubing 204. The annular segment extends over an annular range a between 90° and 110°. This maintains a visual inspectability from an exterior of the device 200 along a significant portion of the perimeter, thereby providing a high degree of user convenience. At the same time, the provision of the electrically conductive section 206 along an annular segment of 100°±10° allows to properly collect or accumulate at least the large majority of the electric charge 212 around the intermediate structure 208.

The tubing 204 has a smooth circular circumference without local protrusions along the entire extension of the tubing 204 so that it can be safely prevented that the tubing 204 unintentionally gets caught or stuck by any other component of liquid separation system 10. In particular, the electrically conductive section 206 is integrally formed with and is embedded within the rest of the tubing 204 in terms of geometry and material with the exception that the carbon black particles are exclusively locally present within the annular segment constituting the electrically conductive section 206.

The device 200 shown in FIG. 2 may be used for instance as a fractionating tube for connecting a flow cell with a fractionating unit of a liquid chromatography apparatus.

Figure 3:
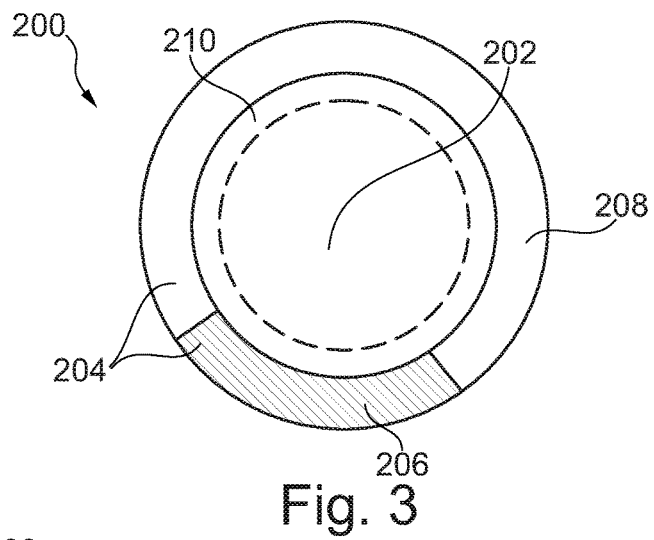

FIG. 3 illustrates a cross-sectional view of an electrostatic discharge protected device 200 for conducting a fluid through a lumen 202 according to another exemplary embodiment of the invention.

The embodiment of FIG. 3 differs from the embodiment of FIG. 2 particularly in that the embodiment of FIG. 3 has the electrically conductive section 206 radially extending the whole way from the lumen 202 to an external surface of the tubing 204. Hence, in other words, the intermediate structure 210 is omitted according to FIG. 3. This has the advantage that the properly electrically conductive material of the electrically conductive section 206 bridges the entire distance between the inner wall of the tubing 204 and an outer wall thereof. Thus, the flow or draining of the electric charge 212 over the tubing 204 is very direct. On the other hand, the embodiment of FIG. 2 has the advantage that the material of the intermediate section 210 may be specifically selected so that any undesired chemical interaction between the liquid solvent and the material delimiting the inner wall of the tubing 204 is avoided or very low.

As indicated with a dotted line in FIG. 3, it is optionally possible that an auxiliary inner tube 210 is placed in the lumen 202 and is connected with the tubing 204 for instance by the application of heat. By taking this measure, it is possible to cover the interior surface of the tubing 200 for with a specifically chemically inert and/or bioinert material to strictly exclude or lower strongly any toxication or contamination of the liquid solvent.

Figure 4:
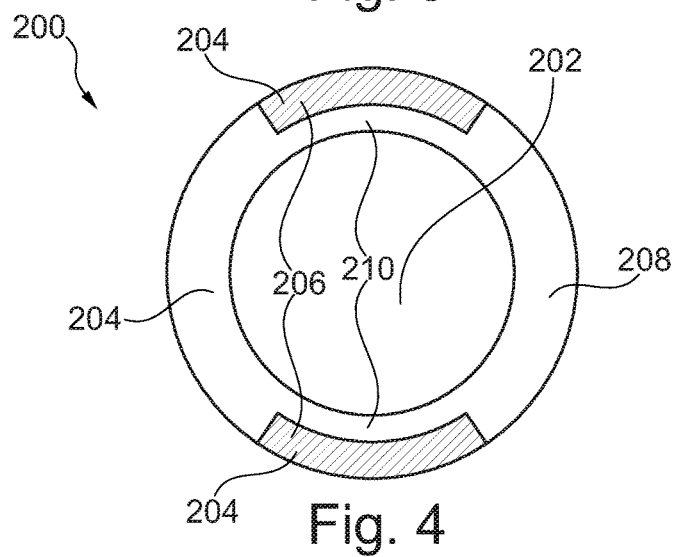

FIG. 4 illustrates a cross-sectional view of an electrostatic discharge protected device 200 for conducting a fluid through a lumen 202 according to yet another exemplary embodiment of the invention.

The embodiment of FIG. 4 differs from the embodiment of FIG. 2 in particular in that in the embodiment of FIG. 4 stacks of an intermediate structure 210 and an electrically conductive section 206 are provided on two opposing annular sections of the tube 204. This further increases the efficiency of transporting electric charge 212 away from an inner surface of the tubing 204. It is clear that any other number of two, three, four or more stacks of an intermediate structure 210 and electrically conductive section 206 may be provided at a corresponding number of annular sections of the tubing 204 in other embodiments, for instance equally distributed along a perimeter of the tubing 204.

Figure 5:
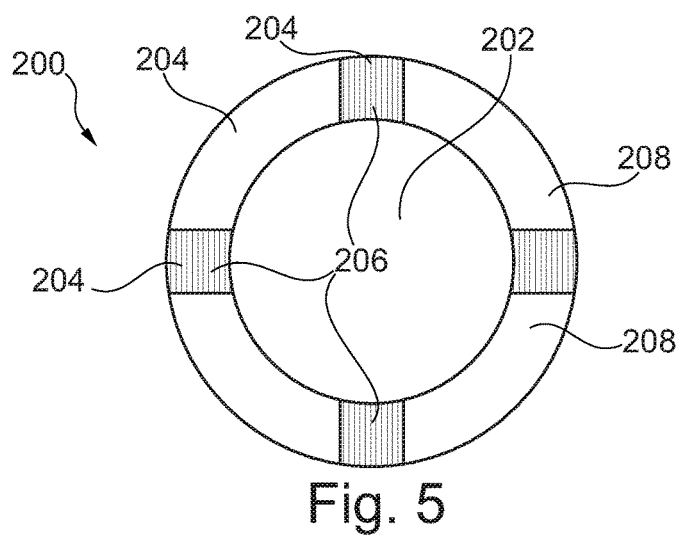

FIG. 5 illustrates a cross-sectional view of an electrostatic discharge protected device 200 for conducting a fluid through a lumen 202 according to an exemplary embodiment of the invention.

The embodiment of FIG. 5 differs from the embodiment of FIG. 3 in particular in that the embodiment of FIG. 5 has four electrically conductive sections 206 which are distributed radially equally with an angular spacing of 90° along a perimeter of the tubing 204. It is clear that any other number of two, three, five or more electrically conductive sections 206 may be distributed radially at a corresponding number of annular sections of the tube 204 in other embodiments.

Figure 6:
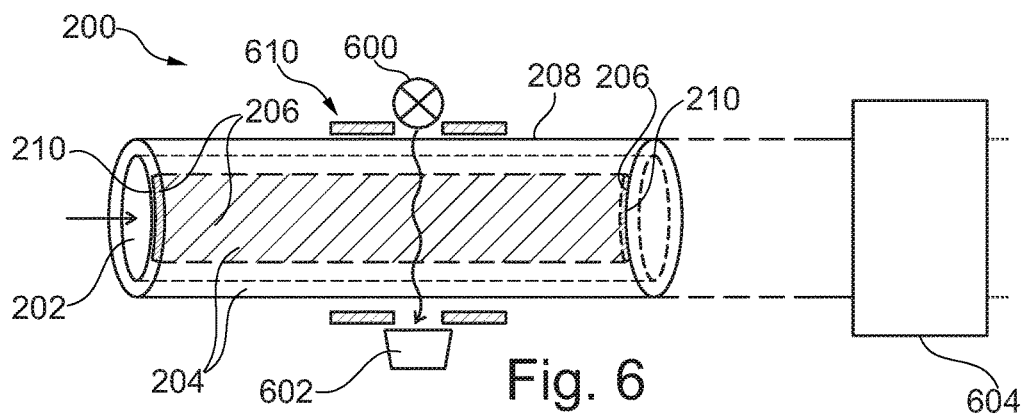
FIG. 6 illustrates a three-dimensional view of a device according to another exemplary embodiment of the invention having an optical detector system and being arranged upstream of a fractioner valve.

FIG. 6 illustrates a three-dimensional view of a device 200 according to another exemplary embodiment of the invention having an optical detector system 610 and being arranged upstream of a fractionating valve 604.

The optical detector system 610 is configured as a refractive index sensor/detector (with all possible wavelengths), a transmission/absorption detector or more specifically a fraction delay detector and comprises a light source 600 for generating primary optical light for propagation through a first part of the optically transparent section 208, the lumen 202, the fluid flowing through the lumen 202, and a second part of the optically transparent section 208. The optical detector system 610 further comprises a light detector 602 arranged for detecting secondary optical light being transmitted through the fluid upon being irradiated with the primary optical light. The optical detector system 610 may hence measure the absorption of light by the fluid.

Figure 7:
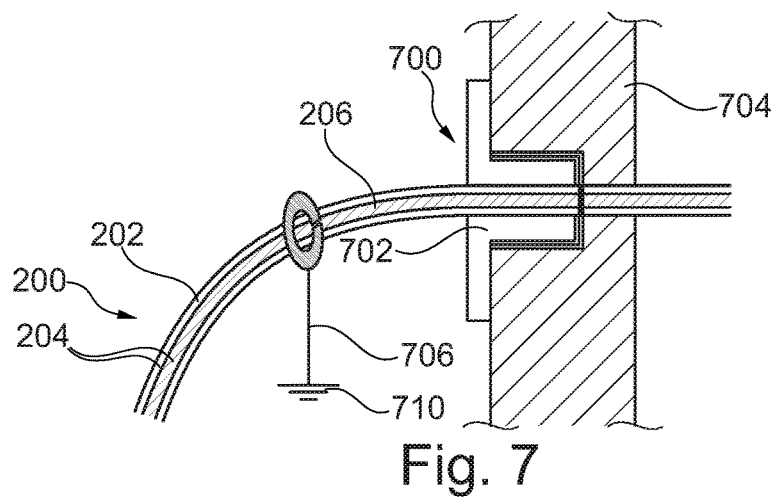
FIG. 7 illustrates a three-dimensional view of a device according to another exemplary embodiment of the invention having a flange with a fitting connected to a housing of a fluidic device.

FIG. 7 illustrates a three-dimensional view of a device 200 according to another exemplary embodiment of the invention having a flange 700 with a fitting 702 connected to a housing 704 of a fluidic device.

The device 200 shown in FIG. 7 comprises a ground connector 706 which is embodied as an electrically conductive ring directly contacting the electrically conductive section 206 of the tubing 204 and which has a direct connection to the electric ground potential, see reference numeral 710. The ground connector 706 is configured to be connected to the electrically conductive section 206 for discharging the electrostatic charge towards ground potential. Moreover, the electrically conductive fitting 702 mechanically couples the device 200 to a grounded housing 704 and simultaneously electrically couples the electrically conductive section 206 to the grounded housing 704. The fitting 702 also provides for a screwing connection between the tubing 204 and the housing 704. Additionally or alternatively, the flange 700 may also connect to the fitting 702, and the fitting 702 (for instance inside or at a bottom) may connect to the housing 704.

Figure 8:
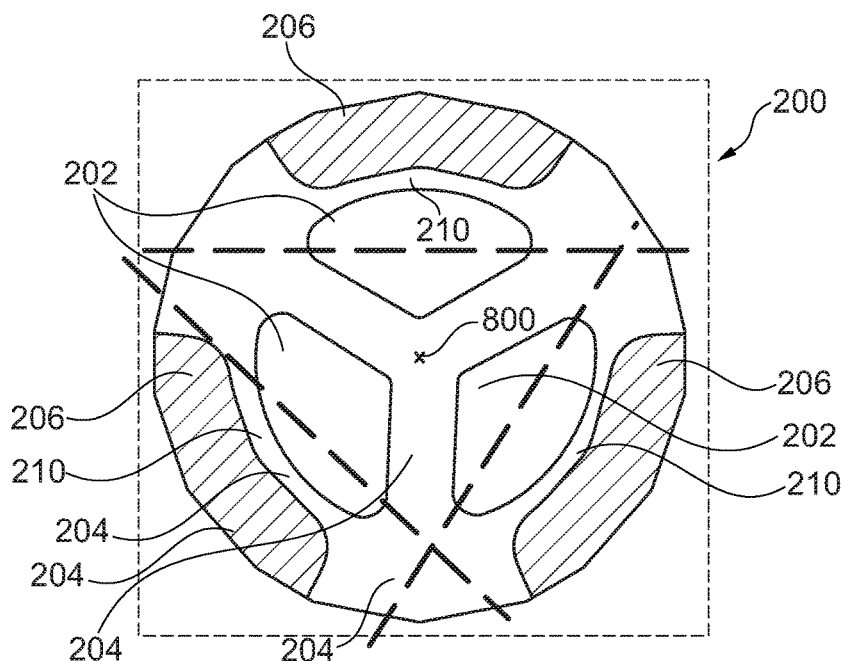
FIG. 8 illustrates a cross-sectional view of a multi-lumen electrostatic discharge protected device for conducting a fluid through one of several lumens according to another exemplary embodiment of the invention.

FIG. 8 illustrates a cross-sectional view of a multi-lumen electrostatic discharge protected device 200 for conducting a fluid through one of several lumens 202 according to another exemplary embodiment of the invention.

The device 200 shown in FIG. 8 comprises three lumens 202, each of which being configured for conducting a separate fluid. Such a device 200 may be used, for instance, for medical applications. For each lumen 202, a separate set of an intermediate structure 210 and an electrically conductive section 206 is foreseen. The three sets of lumen 202, assigned intermediate structure 210 and assigned electrically conductive section 206 are equally distributed around a perimeter of a central axis 800 of the device 200. Hence, the three-lumen tubing 204 has a separate ESD strip for each lumen 202 and is apart from this optically transparent so that a light beam of a light source may propagate exclusively through optically transparent portions of the device 200 so as to be detectable on an opposing side. As can be taken from dashed lines in FIG. 8, the alternating circumferential arrangement of electrically conductive regions and optically transparent regions allows the simultaneous inspection of all lumen 202 via non-interfering optical paths (one path per lumen).

The following table illustrates as to how the embodiments of FIG. 2 and FIG. 3 can provide an efficient electrostatic discharge (ESD) protection, wherein $B^2\pi/4$ is the throughput area of the corresponding tubing. All mentioned tubings were connected with a simple metallic Swagelok system.

| L | B | $B^2\pi/4$ | D | Length | Flow rate (n-hexane) | Material | Voltage |
|---|---|---|---|---|---|---|---|
| 1.6 mm | 0.8 mm | 0.5 mm$^2$ | 0.1 mm | 2 m | 100 mL/min | PTFE/carbon black | 2.0 kV |
| 2.0 mm | 1.2 mm | 1.1 mm$^2$ | 0.4 mm | 1.3 m | 100 mL/min | PTFE/carbon black | 1.1 kV |
| 1.6 mm | 0.8 mm | 0.5 mm$^2$ | — | 2 m | 100 mL/min | PTFE | 3.5 kV |

The first row in the table relates to an embodiment as shown in FIG. 2. The second row in the table relates to an embodiment as shown in FIG. 3 (however, without the auxiliary inner tube 210). The third row in the table, serving as a reference for comparison, relates to a conventional tube consisting of PTFE. As can be taken from the last column of the table, both embodiments of the invention show a significantly better voltage level than the conventional tube. Surprisingly, and under consideration of the fact that the tube relating to the embodiment of FIG. 2 has only about half of the throughput area and has been significantly longer (2 m) than the one according to the embodiment of FIG. 3 (1.3 m), the tube according to FIG. 2 which advantageously has no direct contact between the fluid and the electrically conductive section 206 shows very good properties in terms of electrostatic discharge protection.

It should be noted that the term "comprising" does not exclude other elements or features and the term "a" or "an" does not exclude a plurality. Also elements described in association with different embodiments may be combined. It should also be noted that reference signs in the claims shall not be construed as limiting the scope of the claims.

The invention claimed is:

1. An electrostatic discharge protected device for conducting a fluid through at least one lumen, wherein the device comprises:
    a tubing having a hollow interior defining the at least one lumen;
    wherein the tubing comprises an outer electrically conductive section configured for conducting electric charge, generated within the at least one lumen when the fluid flows through the at least one lumen, away from the at least one lumen,
    wherein the tubing comprises an interior inert section delimiting the entire lumen, the interior inert section forming an intermediate structure separating the at least one lumen from the electrically conductive section, preventing direct contact between the fluid and the electrically conductive section, and configured to conduct electric charge therethrough to the outer electrical section.

2. The device of claim 1, wherein the outer electrically conductive section extends to an outer surface of the tuning so that the electric charge is conducted away from the at least one lumen through at least one part of a wall of the tubing.

3. The device of claim 1, wherein the inert section is configured for electrically conducting the generated electric charge from the at least one lumen through the intermediate structure and towards the electrically conductive section.

4. The device of claim 1, wherein the inert section has, at least at a portion where the chemically inert section is surrounded by the electrically conductive section, a radial thickness (D) in a range between 0.05 mm and 0.4 mm.

5. The device of claim 1, wherein the tubing has a circular or a polygonal outer circumference.

6. The device of claim 1, comprising at least one of the following features:
    at least the part of the material of the tubing which is in direct contact with the fluid conducted through the at least one lumen is chemically inert against a non-polar solvent to be conducted as at least part of the fluid through the at least one lumen;
    the electrically conductive section is integrated or embedded within a wall of the tubing;
    the device comprises a ground connector configured to be connected to the electrically conductive section for discharging the electrostatic charge towards ground;
    the device comprises an electrically conductive fitting system for mechanically coupling the device to a grounded housing and simultaneously electrically coupling the electrically conductive section to the grounded housing;
    an external diameter (L) of the tubing is smaller than 8 mm;
    a thickness (d) of a wall of the tubing is in a range between 0.3 mm and 1.5 mm;
    the electrically conductive section has a value of the ohmic resistance per length of the tubing of less than 2 MΩ/m.

7. The device of claim 1, wherein the interior inert section of the tubing comprises a bioinert material which suppresses fluid dissolution of metal components out from a wall of the tubing.

8. The device of claim 1, wherein the electrically conductive section is configured as an axially extending annular segment of the tubing.

9. The device of claim 8, wherein the annular segment extends over an annular range (α) of angular degrees ranging between 30° and 180°.

10. A fluid separation apparatus for separating a fluidic sample into a plurality of fractions, the apparatus comprising:
    a fluid drive unit configured for driving a fluid comprising a mobile phase and the fluidic sample in the mobile phase along a fluidic path;
    a separation unit arranged within the fluidic path and configured for separating the fluidic sample into the plurality of fractions;
    a device according to claim 1 for conducting the fluid along at least a portion of the fluidic path.

11. The fluid separation apparatus of claim 10, further comprising at least one of:
    a detector configured to detect separated fractions of the fluidic sample;
    a fractioner unit configured to collect separated fractions of the fluidic sample;
    a data processing unit configured to process data received from the fluid separation apparatus;
    a degassing apparatus for degassing the mobile phase.

12. A method of implementing a device according to claim 1 as a fluidic connection downstream of a flow cell of a liquid chromatography apparatus.

13. The method of claim 12, wherein the device is implemented as fluidic connection between the flow cell and a fractioner of the liquid chromatography apparatus.

14. The device of claim 1, wherein the tubing comprises an optically transparent section at least in one or more portions of the tubing, thereby enabling an external inspection of the conducted fluid within the at least one lumen.

15. The device of claim 14, wherein the entire lumen is delimited by the optically transparent section, and wherein the electrically conductive section is arranged to surround part of the optically transparent section so that the electric charge is at least partially electrically conducted from the at least one lumen via the optically transparent section to the electrically conductive section.

16. The device of claim 14, further comprising a light source configured for generating primary optical light for propagation through a first part of the optically transparent section, the at least one lumen, and a second part of the optically transparent section, and further comprising a light detector arranged for detecting secondary optical light being transmitted through the fluid upon being irradiated with the primary optical light.

17. The device of claim 14, wherein at least one of the group consisting of the chemically inert section and the optically transparent section.

18. A method of conducting a fluid, in particular a non-polar fluid, through at least one lumen with electrostatic discharge protection, wherein the method comprises:
   conducting the fluid through a hollow interior of a tubing defining the at least one lumen;
   conducting electric charge, generated within the at least one lumen when the fluid flows through the at least one lumen, away from the at least one lumen by an outer electrically conductive section of the tubing,
   wherein the tubing comprises an interior inert section delimiting the entire lumen, the interior inert section forming an intermediate structure separating the at least one lumen from the electrically conductive section, preventing direct contact between the fluid and the electrically conductive section, and configured to conduct electric charge therethrough to the outer electrical section.

19. The method of claim 18, comprising at least one of the following features:
   the electric charge is conducted away from the at least one lumen through at least a part of a wall of the tubing;
   the fluid comprises or consists of a non-polar solvent;
   the generated electric charge is conducted from the at least one lumen through the intermediate structure and towards the electrically conductive section.

20. The method of claim 18, wherein the interior inert section of the tubing comprises a bioinert material which suppresses fluid dissolution of metal components out from a wall of the tubing.

* * * * *